United States Patent [19]
Uesugi et al.

[11] Patent Number: 5,861,951
[45] Date of Patent: Jan. 19, 1999

[54] PARTICLE MONITORING INSTRUMENT

[75] Inventors: Fumihiko Uesugi; Natsuko Ito, both of Tokyo, Japan

[73] Assignee: NEC Corporation, Tokyo, Japan

[21] Appl. No.: 989,630

[22] Filed: Dec. 12, 1997

[30] Foreign Application Priority Data

Dec. 16, 1996 [JP] Japan .................................... 8-335962
May 21, 1997 [JP] Japan .................................... 9-130985

[51] Int. Cl.[6] .................................................. G01N 21/00
[52] U.S. Cl. ........................................ 356/338; 356/339
[58] Field of Search .................................. 356/336, 338, 356/339, 335, 337, 340–343; 250/574

[56] References Cited

U.S. PATENT DOCUMENTS 5,153,674  10/1992  Bobel et al. ............................ 356/339
5,316,983   5/1994  Fujimori et al. ....................... 356/336

FOREIGN PATENT DOCUMENTS 62-37160   9/1987  Japan .
63-11838   1/1988  Japan .
3-116944   5/1991  Japan .
4-297852  10/1992  Japan .
5-288669   2/1993  Japan .
5-206235   8/1993  Japan .
5-206236   8/1993  Japan .
5-340866  12/1993  Japan .
7-12707    1/1995  Japan .

OTHER PUBLICATIONS

Gary S. Selwyn, "Plasma particulate contamination control. I. Transport and process effects", *J. Vac. Sci. Technol.,* B9 (6), Nov./Dec. 1991, pp. 3487–3492.

Shiratani et al., "In situ polarization–sensitive laser–light-–scattering method for simultaneous . . . particles in plasmas", *J. Vac. Sci. Technol.,* A14 (2), Mar./Apr. 1996, pp. 603–607.

Watanabe et al., "Observation of growing kinetics of particles in a helium–diluted silane rf plasma", *Appl. Phys. Lett.,* 61 (13), Sep. 28, 1992, pp. 1510–1512.

Selwyn et al., "Particle contamination characterization in a helicon plasma etching tool", *J. Vac. Sci. Technol.,* A14 (2), Mar./Apr. 1996, pp. 649–654.

*Primary Examiner*—Hoa Q. Pham
*Attorney, Agent, or Firm*—Sughrue, Mion, Zinn, Macpeak & Seas, PLLC

[57] ABSTRACT

When a intensity of a signal from a light detector 14 to measure a scattered light exceeds a predetermined value, a motion of a particle 20 is displayed as a locus of the scattered light, by means of extending an exposure time of the scattered light to the light detector, or by means of increasing a pulse oscillation frequency of a laser beam 13, or by means of extending a pulse width of the laser light. And then a straight line connecting start and terminal points of the locus is displayed to superimpose on the locus. An origin of the particle is estimated by extending the straight line beyond the start point, and a destination point of the particle is estimated by extending the straight line beyond the terminal point. A mass of the particle is estimated by dividing a projective length of the straight line in a vertical direction by the exposure time of the scattered light.

3 Claims, 5 Drawing Sheets

PARTICLE MONITORING INSTRUMENT

BACKGROUND OF THE INVENTION

1. Field of the Invention

The present invention relates to a particle monitoring instrument which measures particles peeling off from a processing reactor and particles which are appeared and grow and fall down during processing steps, by means of a light scattering method in-situ and in real time.

2. Description of the Related Art

Particles appeared in a processing equipment during manufacturing steps of a large scale integrated circuit (hereinafter referred to as an LSI) are a major cause of reductions in a yield rate of the LSI and the amount of operational time of the processing equipment. In order to prevent the yield and the amount of operational time from being reduced, instruments to monitor the appearance of the particles have been developed.

These instruments are composed of a laser light source and a photodetector and there are two types of instruments, one of which is installed on an exhaust pipe of the processing equipment, and the other absorbs gas from the processing equipment. Both of these pass a sampled fluid through a space where a laser beam exists, and measure an intensity of scattered light whenever particles pass, and the number of the particles appeared. As conventional examples of these instruments, methods disclosed in Japanese Patent Applications Laid Open No. 4-297852/1992, 3-116944/1991, 63-11838/1988, 5-206235/1993, 5-206236/1993, 7-12707/1995, and 5-288669/1993 and Japanese Utility Model Publication No. 62-37160/1987 can be mentioned.

The methods to measure the particles in the sampled fluid involve a problem that the obvious relations between the number of the detected particles and the yield ratio of the LSI, and the relations between the number of detected particles and the amount of operational time of the processing equipment, were not observed. In order to solve this problem, a measurement of the floating particles appeared in the reactor therein in-situ and in real time has been attempted.

Measurement in this attempt is conducted in the following manner. Windows for introducing a laser light into the reactor and for measuring scattered light are fitted on the processing reactor, the laser light scattered by the particles is recorded on a video tape using a CCD camera, the video tape is reproduced to investigate the time for appearance the scattered light and the intensity change thereof, and finally the appearance of the particles can be estimated.

As examples of these conventional methods, there have been papers, here respectively cited, by Gary S. Selwyn, in Journal of Vacuum Science and Technology, Vol. B9, 1991. pp. 3487–3492 and in Vol. A14, 1996. pp. 649–654. Moreover, there have been papers, here respectively cited, by Watanabe et al., in Applied Physics Letters, Vol. 61, 1992. pp. 1510–1512 and by Shiratani et al., in Journal of Vacuum Science and Technology, Vol. A14, 1996. pp. 603–607.

The foregoing conventional technologies involve the following problems.

In the technologies disclosed in Japanese Patent Applications Laid Open No. 4-297852/1992, 3-116944/1991, 63-11838/1988, 5-206235/1993, 5-206236/1993, 7-12707/1995, and 5-288669/1993 and Japanese Utility Model Publication No. 62-37160/1987, which are mentioned as the conventional examples, the methods to measure the particles in the sampled fluid are described. Since these methods adopt measuring the scattered light in sampled fluid, it is difficult to specify the origin of the particles. Therefore, there is a problem that it is difficult to obtain a relation between the amount of operational time of the equipment and the amount of appeared particle and a relation between a yield ratio of the LSI and the amount of appeared particle.

In the papers that are respectively cited, by Gary S. Selwyn, in Journal of Vacuum Science and Technology, Vol. B9, 1991. pp. 3487–3492 and in Vol. A14, 1996. pp. 649–654, by Watanabe et al., in Applied Physics Letters, Vol. 61, 1992. pp. 1510–1512 and by Shiratani et al., in Journal of Vacuum Science and Technology, Vol. A14, 1996. pp. 603–607, the particles floating in the processing reactor are detected by the laser light scattering method, and measured spatial distribution of the particles and its change with time. However, it is difficult to know whether the observed particles cause the faults on wafers, to know the origin of the particles and to know which paths the particles travel to reach a wafer. For these reasons, the origin of the particles causing defective patterns on a wafer product can not be specified. Therefore portions and parts of the processing equipment to require the reform can not be recognized. And the measurement of particle appearance has been cleaning of the equipment. Specifically, there has been no policy to inhibit the appearance of the particles, so that the amount of operational time of the processing equipment cannot be improved owing to cleaning of the reactor and preparative operation.

When the measurement of the spatial distribution of the particles, the way of detecting particles adopts either the laser light scanned spatially or the laser light expanded spatially. In this case, distances from places where laser light scattering occur to the detector are different, and intensities of the scattered lights at the detector is inversely proportional to a square of the distance from the scattering point to the detector. Specifically, to estimate the particle size from the intensity of the scattered light, it is necessary to correct the intensity of the scattered light depending on the distance. However, such correction has not heretofore been performed.

Moreover, to estimate the particle size form the intensity of the scattered light, it is assumed that the shape of the particle is perfectly spherical. However, it has been known that many of the particles appeared on LSI manufacturing steps are in a flasky form and in a needlelike form. For the particles of such shapes, the intensity of the scattered light greatly depends on an arrangement of a direction of incident beam and particle. Therefore, by the estimation of the particle size assuming a perfect sphere particle, errors of a particle size, a distribution of particle size, and a numerical density of the particles become large.

Currently spatial distribution of the particles using the light scattering method is measured as follows. A specifically polarized light is introduced into the processing reactor and the changes of the polarization of the light scattered by the floating particles are measured. Only one wavelength of the light from the light source used is used. When a size of the observed particle is smaller than the wavelength of the irradiation light, the intensity of the scattered light is estimated with a Rayleigh scattering formula. When the size of the particle is larger than the wavelength of the irradiation light, a Mie scattering formula is employed. Although the Mie scattering formula gives a strict solution, its equation is complicated so that a long time is required for a numerical calculation. Therefore no positive information on the size and numerical density of particles, is available on real time, from the results of the scattered light intensity measurements.

SUMMARY OF THE INVENTION

The object of the present invention is to provide a particle monitoring instrument which is capable of easily estimating an origin, a destination point, and a mass of a particle, correcting a change of a scattering light intensity depending on a distance from the scattered point to a detector in order to estimate a particle size, enlarging range of the particle size to which a Rayleigh scattering formula is allowed to apply for simple numerical calculation, and precisely estimating the particle size by estimating a shape of the particle.

In a first aspect, the particle monitoring instrument of the present invention comprises means for introducing a laser light into a processing reactor and means for measuring scattered light by the particle; the particle monitoring instrument further comprising means for displaying a motion of the particle as a locus of the scattered light by prolonging an exposure time of a light detector, by making a pulse repetition frequency of the laser light higher, or by widening the pulse width of the laser light, when an intensity of a signal from the light detector to measure the scattering light exceeds a predetermined value; and means for displaying a straight line connecting a start point and an end point of the locus and superposing it on the locus, stretching the straight line beyond the starting point to estimate an appearance point of the particle, stretching the straight line beyond the end point to estimate a destination point of the particle, and dividing a projective length of the straight line in a vertical direction by the exposure time of the scattered light to estimate a mass of the particle.

In a second aspect, the particle monitoring instrument of the present invention comprises means for introducing a laser light into a processing reactor and means for measuring a scattered light by a particle; the particle monitoring instrument further comprising means for rotational reciprocating a mirror within a range of a predetermined rotation angle set in front of a laser light source to scan the laser light fanwise over a wafer surface in horizontal or vertical plane, the mirror being disposed in front of a laser light source, means for having one to one corresponding between the rotation angle of the mirror from a mirror rotation controller to a data processor and the signal of the scattered lights from the light detector, means for converting all of the intensities of the scattering lights into the intensities on the datum line which is a center line of the laser light and vertical to the light detector by a relative formula among a mirror rotation angle, a distance from a datum line to the light detector, a distance of the line intersecting at the right angle with the datum line from a scattered point of the particle to the light detector, and a distance from the refracted point on the mirror to a point of intersection of the datum line from the scattered point of the light on the datum line.

In a third aspect, the particle monitoring instrument of the present invention comprises means for introducing a laser light into a processing reactor and means for measuring a scattered light by a particle, the particle monitoring instrument further comprising means for moving in parallel a mirror set in front of a laser light source to scan the laser light in band-sharp over a surface of a wafer in horizontal or vertical plane, means for having one to one correspondence between a position of the mirror from a mirror motion controller to a data processor and the signal of the scattered lights from the light detector, and means for converting all of the detected intensities of the scattering lights into the intensities on a datum line which is a center line of the laser light from a relative formula among a velocity of the mirror, an elapsed time from the time when the laser light is at the datum line, a distance from the datum line to the light detector, a distance of the line intersecting at the right angle with the datum line from a scattered point of the light to the light detector.

In a fourth aspect, the particle monitoring instrument of the present invention comprises means for introducing a laser light into a processing reactor and means for measuring a scattered light by a particle;

the particle monitoring instrument further comprising means for estimating a size of a particle, or a numerical density of the particles or a refractive index from an intensity of the scattered light, means for calculating parameter depending on the size of the particle and a wavelength of the laser light and means for enlarging, a range of the particle size to which a Rayleigh scattering formula is applicable by making a wavelength of the laser light longer, when the particle diameter exceeds a predetermined value.

In a fifth aspect, the particle monitoring instrument of the present invention comprises means for introducing a laser light into a processing reactor and means for measuring a scattered light by a particle, the particle monitoring instrument further comprising means for displaying the scattered light by a falling particle as a locus or a sequence of dots by irradiating the laser light in a form of a series of pulse and measuring the scattered light to expose a light detector for the time equal to from several to several tens of pulses and means for estimating a shape of the particle by tracking the locus of the scattered light during a predetermined time, and analyzing a change of an intensity of the scattered light depending on time or a ratio of a maximum intensity of the scattered light and a minimum value.

To describe more fully, the means for assuming the shape of the particle spherical when a change of an intensity of the scattered light or the ratio of the maximum intensity of the scattered light and the minimum value is smaller than the predetermined value, and assuming the shape disk-shaped when the change of the intensity of the scattered light or the ratio of the maximum intensity of the scattered light and the minimum value is larger than the predetermined value, and means for estimating an area of a disk from the maximum intensity of the scattered light and a thickness of the disk from the minimum intensity of the scattered light, when the shape of the particle is estimated to be disk-shaped.

The summary is follows; the particle monitoring instrument of the present invention has abilities to easily estimate the appearance and destination points of the particle and the mass, to correct the intensity change of the scattered light depending on the distance in order to estimate the particle size, to enlarge the range of the particle size to which the Rayleigh scattering formula is applicable, and to accurately estimate the particle size by estimating the shape of the particle.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION OF THE PREFERRED EMBODIMENTS

Figure 1:
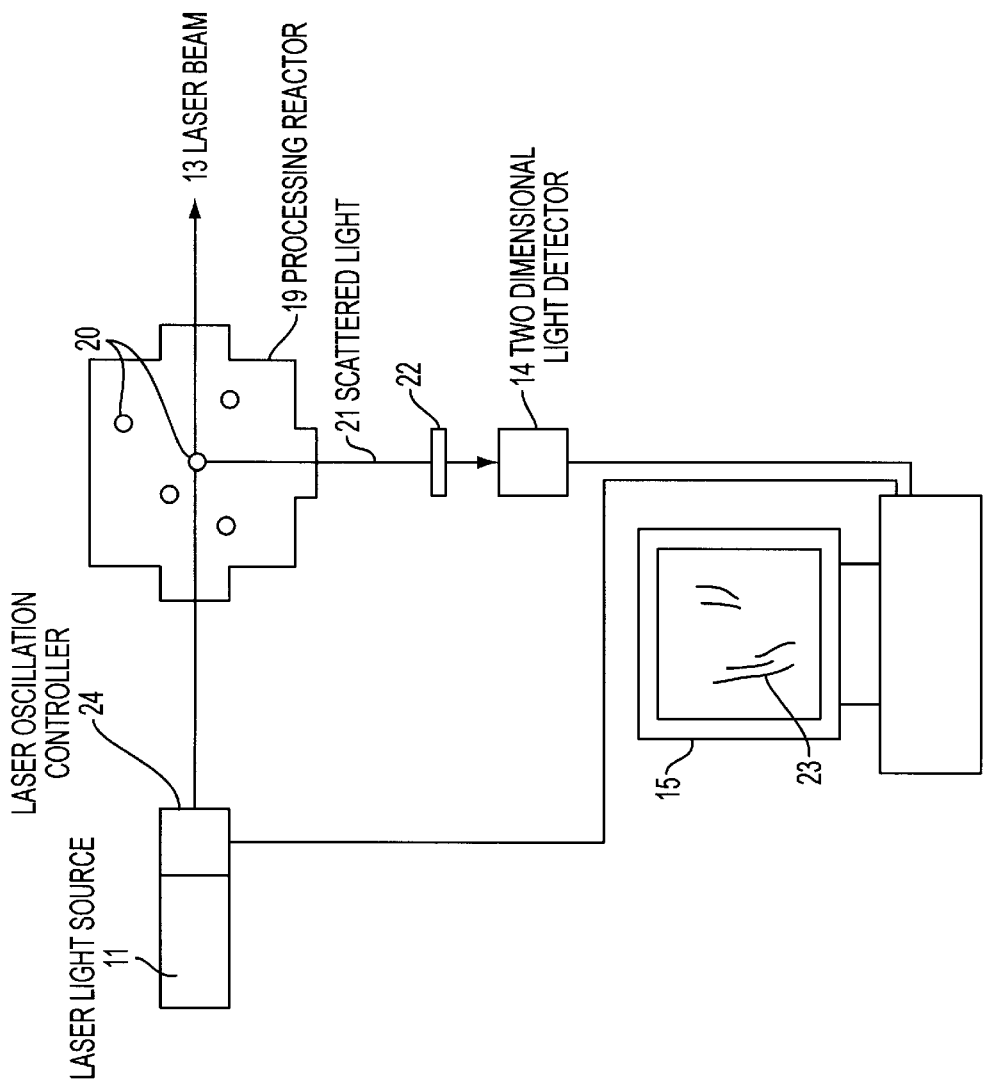
FIG. 1 shows a schematic constitution of an instrument to obtain a locus of a scattered light, which is a first embodiment of the present invention.

Next, embodiments of the present invention will be described with reference to the accompanying drawings.

First Embodiment

In order to estimate an origin of a flaking particle and a destination point of the particle onto a wafer, an only momentary measurement of a scattered light by the particle is insufficient, and a tracking of the scattered light for a specified time is required. Therefore, when an intensity of the scattered light by the particle is over predetermined value, an exposure time of a scattered light detector is prolonged, a repetition frequency of a laser is made pulse higher, or, a chopping frequency of a CW laser (Continuous Wave laser) is made lower to acquire a two-dimentional image of the scattered light.

By using these methods, the locus of the scattered light from the particle falling down can be displayed, and an origin and a destination place can be estimated from a start point and a terminal point of the locus. Moreover, a mass of the particle can be estimated by dividing a length of the locus by a time for measuring.

Estimation method of the origin of the particle and its destination position on a wafer will be described with reference to FIG. 1.

A laser light source 11 consists of a YAG laser and a secondary harmonic wave light generator. The oscillation frequency of laser light is 10 Hz. Laser light 13 has a wavelength of 532 nm and laser beam is shaped into a sheet form in a vertical plane. Thereafter, the laser light is introduced into a processing reactor 19. The laser light 13 is scattered by particles 20, which are floating or falling down in the processing reactor 19. A scattered light 21 passes though an interference filter 22 and it is measured every 5 s for a gate opening time 100 ns by a two dimensional light detector 14. The spatial distribution of scattered light is displayed in a data processor 15.

The data processor 15 judges whether the two dimensional light detector 14 receives a scattered light intenser than a predetermined value. If the light detector 14 receives the scattered light intenser than that value, an exposure time of the two dimensional light detector 14 is prolonged to 200 ns by prolonging the time of opening the gate, an a motion of the particle is acquired as a locus 23 of the scattered light. The same effect can be obtained by measuring at 1 second interval instead of prolonging the time for opening a gate.

For the same purpose, it can be used that a frequency of laser light scattering is raised by an increase of an oscillation frequency of the laser from 10 Hz to 10 KHz with an oscillation controller 24, instead of prolonging the exposure time of the scattered light by changing the time for the gate opening or the intervals of the measurement. In case of a CW laser, a chopper for pulsing of a laser light 13 is used instead of the laser oscillation controller 24. By extension of a pulse width with low rotational speed of a chopper, the same effect can be obtained.

Using the method, it can show the scattered light on a display unit of the data processor 15 as the locus 23. And a straight line connecting start and terminal points of the locus 23 is displayed over the locus 23 superposing. And by means of extension of the straight line from the start point, an origin of the particle can be estimated. Moreover, by means of extension of the straight line from the terminal point, a destination point of the particle can be estimated. By means of the amount of when a projective length of the straight line in the vertical direction divided by the exposure time of the scattered light, a mass of the particle can be estimated.

As described above, by measuring the locus of the scattered light, the origin and destination point of the particle and its mass can be estimated so that a guide to select materials for the reactor and to design a shape of the reactor, in order to reduce the appearance of the particle, can be offered.

Second Embodiment

Figure 2:
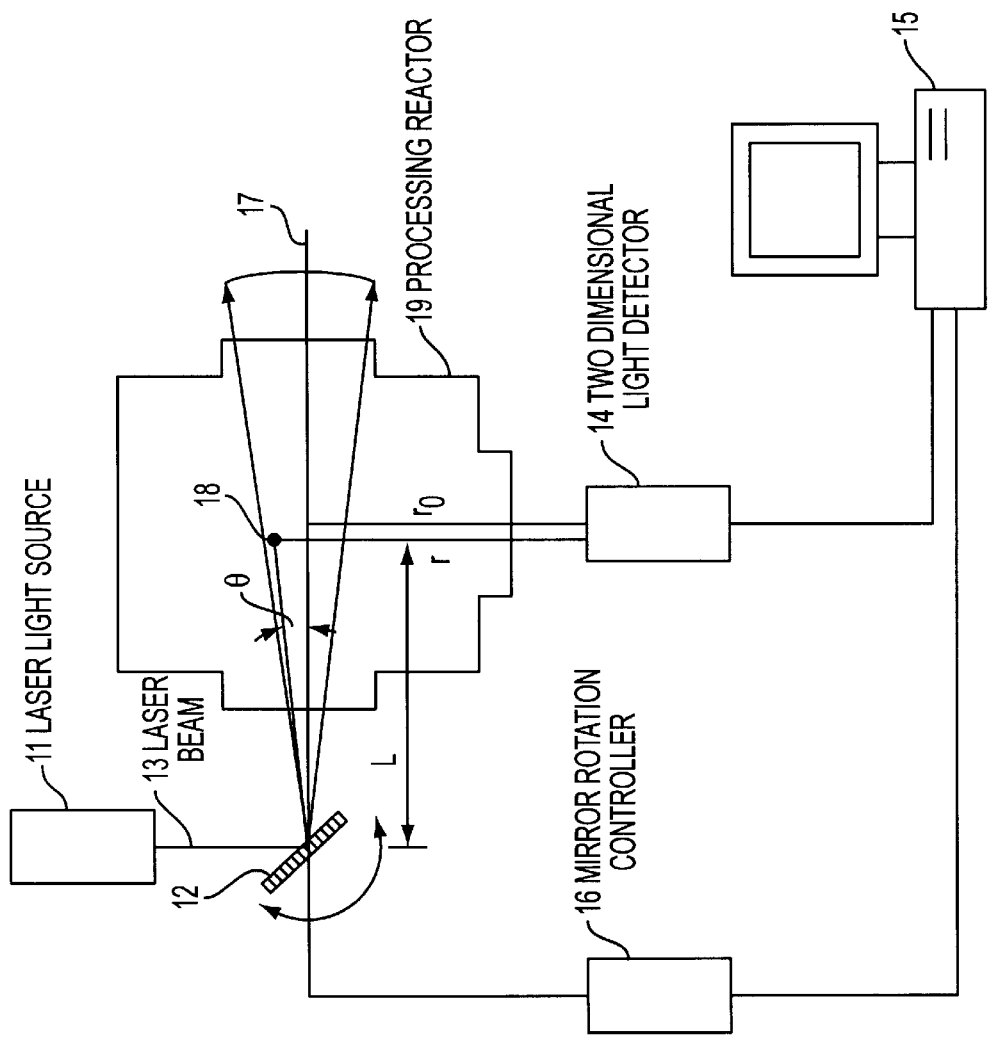
FIG. 2 shows a schematic constitution of an instrument to correct an intensity of a scattered light, which is a second embodiment of the present invention.

An intensity of the scattered light relates to a particle size. On the other hand, the intensity of the scattered light is inversely proportional to a square of a distance between a scattering point and a measurement point. Specifically, the intensities of the scattered lights by the particles of the same size are equal. Although distances between the measurement point and the scattering point differ, the intensities of the scattered light by the particles of the same size are measured in different value. Therefore, in order to estimate a particle size form the two dimensional image of the intensity of the scattered light, the intensity of the scattering light must be collected to the value at same distance. A way to realize this will be described with reference to FIG. 2.

A laser light source 11 consists of a YAG laser and the secondary harmonic light generator. An oscillation frequency is 10 kHz. The wavelength of laser beam 13 is 532 nm. The laser beam 13 is reflected by a mirror 12 and introduced into the inside of a processing reactor 19. The mirror 12 performs rotational reciprocating between the left and right of the center line 17. The maximum rotation angle is 10 degrees. And the laser beam 13 reflected by the moving mirror 12 scans fanwise in a horizontal plane over the surface of wafer. When a particle exists in a range of view of the two dimensional light detector 14, a spatial distribution of the scattered light by the particle is obtained. When the spatial distribution of the scattering light is displayed in the data processor 15, the intensity of the scattered light is corrected in the following manner. A rotation angle θ is transferred to the data processor 15 from the mirror rotation controller 16. Each of scattered lights is detected by the elements of the two dimensional light detector 14, in the position corresponding to the position where the light is scattered.

The intensities of the scattered lights detected by the elements of the detector 14 depends on distances. The intensity I of the scattered light takes the form of the following formula in either Rayleigh scattering or Mie scattering.

$$I = F/r^2$$

where F is a function of the particle size, a numerical density of the particles and a refractive index. The center line 17 shall be a datum position of the laser beam 13. r is used for a distance from the center line 17 serving as the datum position to the two dimensional light detector 14, and r is used for a distance of a perpendicular from the scattering position 18 on the center line 17 to the two dimensional light detector 14. L is used for a distance between the reflective point of the mirror 12 and the point of intersection of the perpendicular line from the scattering position 18 to the center line 17. There is the following relation between these distance and the angle.

$$r = r_0 + L \# \tan \theta$$

For either the Rayleigh or the Mie formula, If $r_0$ is used for the distance in the formula to calculate the intensity of the scattered light, all of the intensities of the scattered lights are converted to intensities on the center line 17. As a result, a particle size and a numerical density of the particles can be compared with others by comparison of the intensities of scattered light.

Third Embodiment

Figure 3:
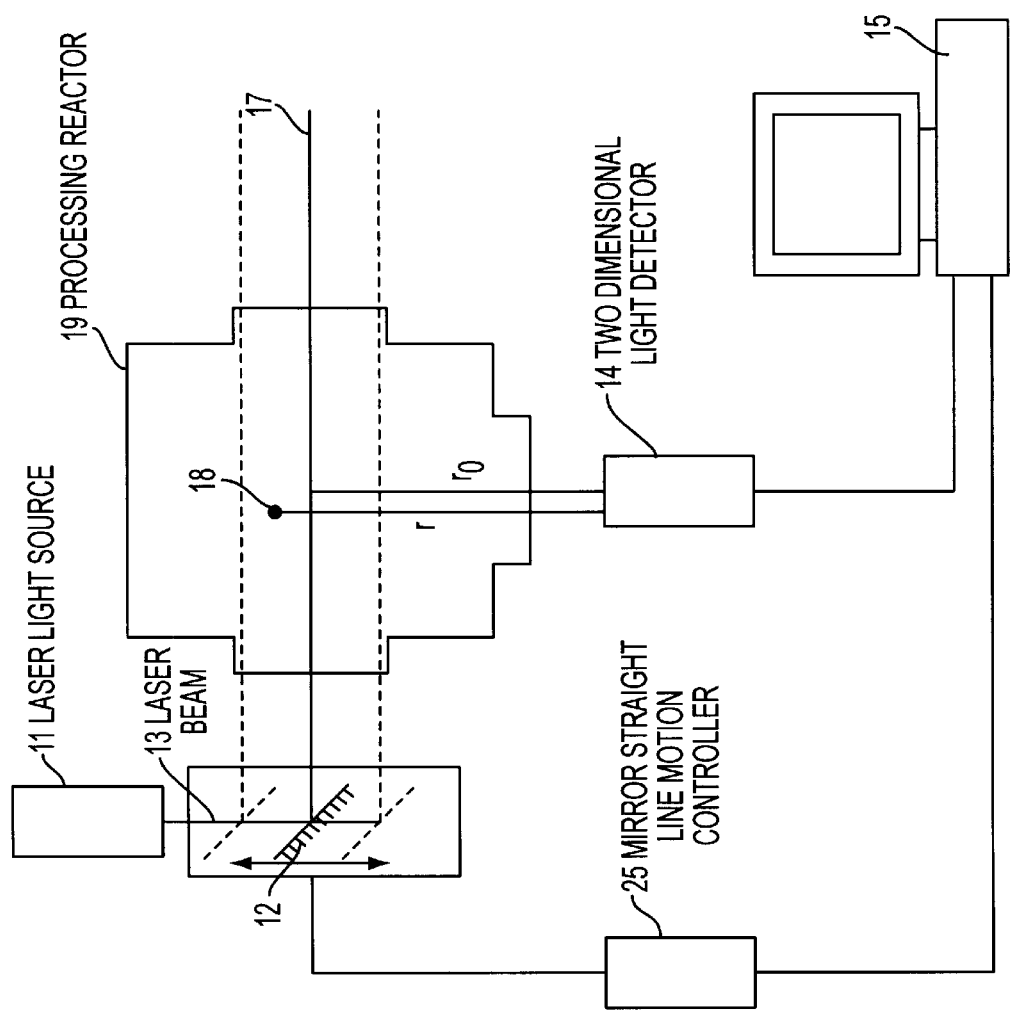
FIG. 3 shows a schematic constitution of an instrument to correct an intensity of a scattered light, which is a third embodiment of the present invention.

Another method to correct an intensity of a scattered light in this embodiment is described with reference to FIG. 3. A mirror 12 is moved in parallel, to scan a laser light 13 into a band-shaped in the horizontal plane. The laser light source, wavelength and oscillation frequency used are the same as those in the second embodiment.

When a spatial distribution of the scattered light is displayed on a data processor 15, an intensity of the scattered light is corrected in the following manner. The position data of the mirror 12 is transferred to the data processor 15 from a mirror straight line motion controller 25. Each of scattered lights is detected by the elements of the two dimensional light detector 14 in the position corresponding to the position where the light is scattered. The intensity of the scattered light detected by each of the elements depends on the distance. The intensity of the scattering light is expressed with the following formula in either the Rayleigh or the Mie scattering, $$I = F/r^2$$

where F is a function of the particle size, a numerical density of the particles and a refractive index. In order to correct a distance r between a point 18 where laser beam is scattered and the two dimensional light detector 14, a distance from the particle to the detector is used for $r = r0 \pm vt$, where v is a motion speed of the mirror 12 and t is an elapsed time for the mirror to move from the center line 17. By means for a calculation using r, the intensity of the scattered light is converted to the value on the center line 17. As a result, particle size and a numerical density of the particles can be compared.

In the second and third embodiments, the case where the laser light is scanned in the form of the sheet in the horizontal plane was described. However, a case where the laser light is scanned in the form of the sheet in the vertical plane may be adopted.

Fourth Embodiment

Next, when a diameter of the particle and a numerical density of the particles are estimated from an intensity of a scattered light, a numerical calculation is simple in a range of the particle size where the Rayleigh scattering formula can be applied. However, in a range of the large particle size where the Mie scattering formula must be applied, a vast amount of time is required to perform a numerical calculation. In order to solve such a problem, when an intensity of the scattered light from the particle becomes greater than a predetermined value, a wavelength of a laser beam is made longer into a range of the particle size where the Rayleigh scattering formula can be applied. When a parameter of the particle size ($x = 2 \pi a/\lambda$, where a is a radius, and $\lambda$ is a wavelength of the light) is about 0.7 or more, the intensity calculated with the Rayleigh formula becomes larger by about 5% than a true value estimated with the Mie formula. When the parameter x becomes equal to 0.7 or larger than a predeterminated value during data processing to calculate numerically for the particle size and the numerical density of the particles using a Rayleigh scattering cross section, a wavelength of the laser light is changed to a longer wavelength to make the parameter x smaller, so that the Rayleigh scattering formula may always be applied.

Figure 4:
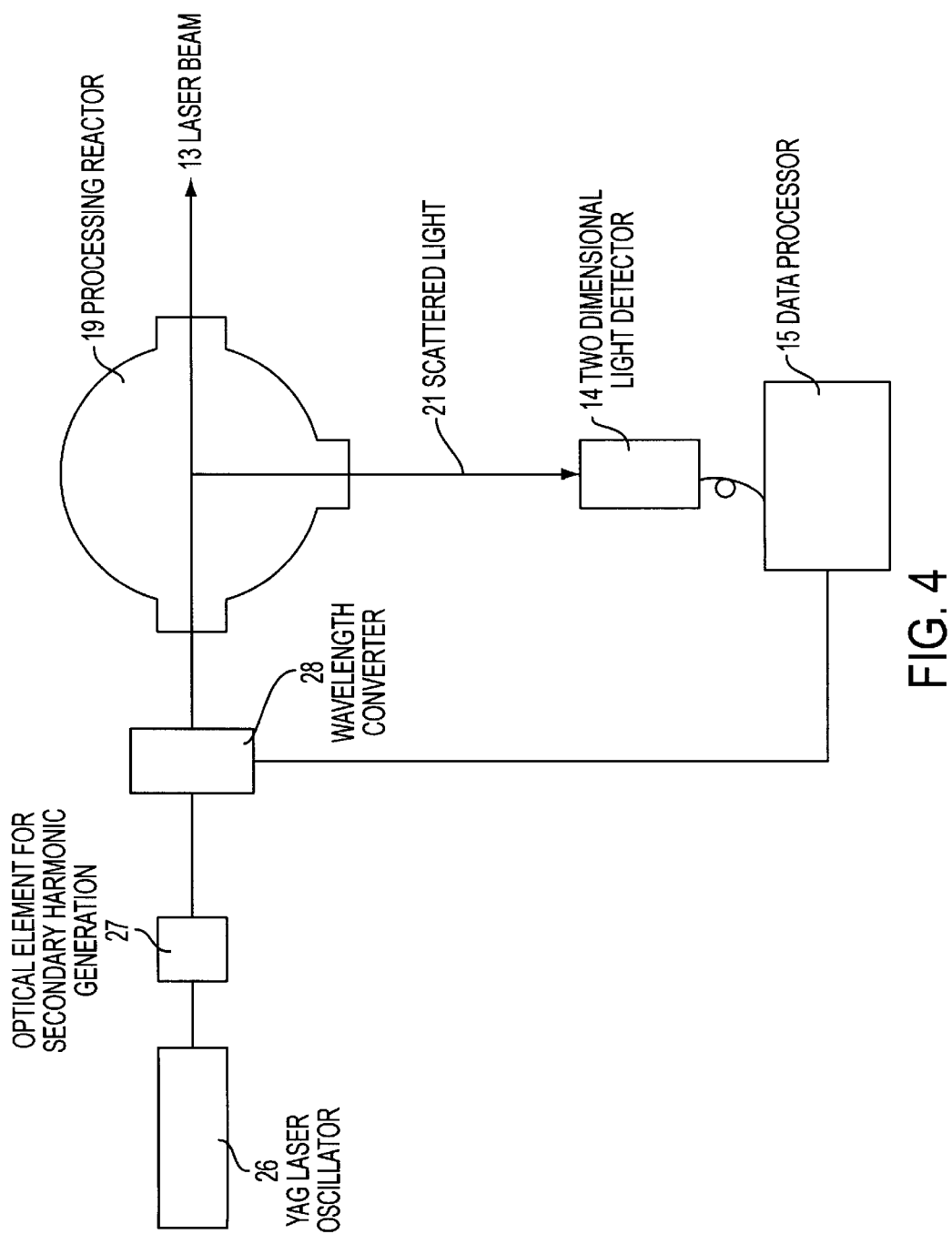
FIG. 4 shows a schematic constitution of an instrument for measuring a scattered light in a region of the particle size, to which a Rayleigh scattering formula is applicable, which is a fourth embodiment of the present invention.

When the particle size, a numerical density of the particles and a refractive index are made an estimate based on two dimensional image of the intensity of the scattered light, an instrument can be calculated numerically using the Rayleigh scattering formula which is comparatively simple. A constitution of the instrument is described with reference to FIG. 4.

A laser light of 1.064 μm from a YAG laser oscillator 26 is irradiated onto an optical element 27 for secondary harmonic generation and a 532 nm light is generated. A wavelength converter 28 is attached to an output side of the optical element 27 for secondary harmonic generation. Wavelength converter 28 switches to either the fundamental wave light 1.064 μm or the 532 nm light from YAG laser oscillator 26 with a signal from a data processor 15. And the wavelength converter 28 introduces laser beam into an processing reactor 19. At first, the 532 nm light is introduced into an processing reactor 19. The scattered light by particles 21 passes through some optical elements, and it reaches a two dimensional light detector 14. A signal from the detector 14 is calculated numerically by the data processor 15, and the information of the particle size and a numerical densities of the particles can be obtained.

Figure 5:
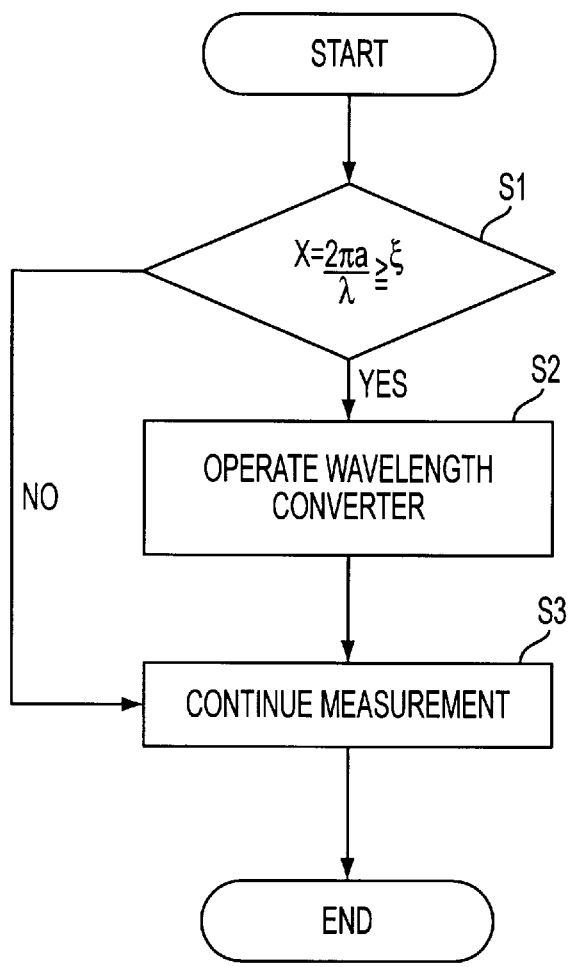
FIG. 5 shows a flow chart of data processing algorithm to calculate a correction value numerically in the applicable region of Rayleigh scattering formula, which is used in the fourth embodiment of the present invention.

In an algorithm of the data processing performed in the data processor 15, a step (S1) for comparison between the parameter x and a predeterminated value $\xi$ is inserted as shown in FIG. 5. If $X \geq \xi$ is satisfied, the secondary harmonic wave light 532 nm is cut off and the fundamental wave light 1.064 μm is used (S2) by wavelength converter 28. On the other hand, if $X < \xi$ is satisfied, the secondary harmonic wave light 532 nm keeps being used to measure (S3). Establishing $\xi$ to 0.7, the numerical calculation using the Rayleigh formula can be executed with a precision of less than 10%.

By introducing these steps, the data processing not to put too much load to the data processor 15 can be realized under the experimental conditions where the Rayleigh formula can be always applied.

In this embodiment, an example to switch the fundermental wave light and the secondary harmonic wave light is described. As another method, using an argon ion laser, which can emit plural wavelength lights, the wavelength is changed to the longer wavelength by a grating whenever it is judged that $X \geq \xi$ is satisfied. As another method, using plural laser light sources, which emit laser lights of different wavelengths, the laser light source oscillating at a longer wavelength is used whenever it is judged that $X \geq \xi$ is satisfied. Moreover, it is unnecessary to fix the value of $\xi$ to 0.7, it may be variable according to a requisite precision.

Fifth Embodiment

When the particle is disk-shaped or needle-shaped, an intensity of a scattered light depends on an angle between a particle axis direction and a direction of an incident laser light. By means of tracking a locus of the scattered light during an established time, and analyzing of the intensity change with time, a shape of the particle can be estimated. Moreover, a size of the particle can be more precisely estimated from maximum and minimum values of the intensity of the scattered light.

In this embodiment, a constitution of an instrument is described, in which a shape of the particle is estimated to correct a particle size, a numerical density of the particles, and a refractive index by basing on two dimensional image of the intensity of the scattered light.

Similar to the first embodiment shown in FIG. 1, a laser light source 11 consists of a YAG laser and a laser oscillation controller 24. An oscillation frequency is 10 Hz. A laser beam 13 has 532 nm wavelength, and a laser beam is shaped to be sheet-shaped in a vertical plane, and it is introduced into a processing reactor 19. The laser beam 13 is scattered by a particle 20 which is floating or falling down in the reactor 19. The scattered light 21 passes through an interference filter 22, and is measured by a two dimensional light detector 14 at Is interval within exposure time of 100 ns. A spatial distribution of scattered light is displayed on a data processor 15. In such manner described above, a motion of the particle is acquired as a locus 23 of the scattered light, the locus 23 having continuous bright points.

If the particle falling down in a vertical direction is spherical, the intensity I of the scattered light never changes whatever the direction the particle takes with respect to a direction of the incidence laser light. On the other hand, if the particle is disk-shaped, the intensity I of the scattered light greatly changes depending on the direction of the particle with respect to the direction of the incidence laser light. For this reason, when the intensity change ratio $\zeta$ of the bright points consisted to locus is less than 50%, the particle is determined to be spherical, and a particle size is estimated by applying the Rayleigh scattering formula or the Mie scattering formula. On the other hand, the intensity change ratio $\zeta$ of the bright points is equal 50% or more, the particle is determined to be disk-shaped, and an area of the disk of the particle is estimated from the maximum intensity of the scattered light and a thickness is estimated from the minimum intensity of the scattered light.

A standard of judgment of the particle shape is not only based on the intensity change ratio $\zeta$ of the continuous bright points consisted to the locus 23, but also it may be set by a ratio $\delta$ of the maximum intensity and the minimum intensity. Moreover, the value of the intensity change ratio $\zeta$ need not be fixed to 50%, and it may be set by changing the value according to a requisite precision.

As described above, by the particle monitoring instrument of the present invention using the light scattering method, the appearance and destination points of the particle and the mass are easily estimated, the intensity change of the scattered light depending on the distance can be corrected to estimate the particle size, the range of the particle size where the Rayleigh scattering formula can be applied is expanded for a simple numerical calculation, and the particle size can be estimated precisely by estimating the shape of the particle.

Therefore, the present invention can give a guide to improve the selection of the materials for the reactor and the shape of the reactor to decrease the appearance of the particle.

Although the preferred embodiment of the present invention has been described in detail, it should be understood that various changes, substitutions and alternations can be made therein without departing from spirit and scope of the invention as defined by the appended claims.

What is claimed is:

1. A particle monitoring instrument comprising:

means for introducing a laser light into a processing reactor;

means for measuring a scattered light by a particle;

means for displaying a motion of said particle as a locus of said scattered light by prolonging an exposure time of said scattered light when an intensity of a signal from said light detector to measure said scattered light exceeds a predetermined value; and means for displaying a straight line connecting start and terminal points of said locus on said locus, estimating an origin of said particle by extending said straight line beyond said start point, estimating a destination point of said particle by extending said straight line beyond said terminal point, and estimating a mass of said particle by dividing a length obtained by projecting said straight line in a vertical direction by said exposure time of said scattered light.

2. A particle monitoring instrument comprising:

means for introducing a laser light into a processing reactor;

means for measuring a scattered light by a particle;

means for displaying a motion of said particle as a locus of said scattered light, by increasing a pulse oscillation frequency of said laser light source, when an intensity of a signal from a light detector to measure said scattered light exceeds a predetermined value; and means for displaying a straight line connecting between start and terminal points of said locus on said locus, estimating an origin of said particle by extending said straight line beyond said start point, estimating a destination point of said particle by extending said straight line beyond said terminal point, and estimating a mass of said particle by dividing a length obtained by projecting said straight line in a vertical direction by an exposure time of said scattered light.

3. A particle monitoring instrument comprising:

means for introducing a laser light into a processing reactor;

means for measuring a scattered light by a particle;

means for displaying a motion of said particle as a locus of said scattered light by prolonging a pulse width of said laser light, when an intensity of a signal from a light detector to measure said scattering light exceeds a predetermined value; and means for displaying a straight line connecting between start and terminal points of said locus on said locus, estimating an origin of said particle by extending said straight line beyond said start point, estimating a destination point of said particle by extending said straight line beyond said terminal point, and estimating a mass of said particle by dividing a length obtained by projecting said straight line in a vertical direction by an exposure time of said scattered light.

* * * * *